United States Patent [19]
Hsieh

[11] Patent Number: 5,974,109
[45] Date of Patent: Oct. 26, 1999

[54] METHODS AND APPARATUS FOR CELL GANGING IN A MULTISLICE COMPUTED TOMOGRAPHY SYSTEM

[75] Inventor: Jiang Hsieh, Waukesha, Wis.

[73] Assignee: General Electric Company, Milwaukee, Wis.

[21] Appl. No.: 08/965,821

[22] Filed: Nov. 7, 1997

[51] Int. Cl.⁶ .................................. A61B 6/03; G01T 1/16
[52] U.S. Cl. ................................................ 378/19; 378/901
[58] Field of Search .................... 250/363.02, 370.09; 378/4, 19, 901

[56] References Cited

U.S. PATENT DOCUMENTS 5,430,784  7/1995  Ribner et al. ............................. 378/19
5,822,392  10/1998  Hedengren ............................. 378/98.8

*Primary Examiner*—David Vernon Bruce
*Attorney, Agent, or Firm*—John S. Beulick; Christian G. Cabou; Phyllis Y. Price

[57] ABSTRACT

A combination of double and triple cell ganging which resolves any incompatibility between the number of detector channels and the lower number of DAS channels without requiring any significant hardware and software changes is described. In one specific embodiment, at least some detector cells on one side of the detector outside the FOV are wired in pairs, i.e., ganged, to form a set of 2 mm channels, and on the other side of the detector outside the FOV, at least some detector cells are wired together, i.e., ganged, to form a set of 3 mm channels. Such ganging of detector cells avoids having to make any significant hardware and software changes to known multislice CT systems.

17 Claims, 2 Drawing Sheets

METHODS AND APPARATUS FOR CELL GANGING IN A MULTISLICE COMPUTED TOMOGRAPHY SYSTEM

FIELD OF THE INVENTION

This invention relates generally to computed tomography (CT) imaging and more particularly, to detector configuration and image reconstruction in a CT system.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Multislice CT systems are used to obtain data for an increased number of slices during a scan. Known multislice systems typically include detectors generally known as 2-D detectors. With such 2-D detectors, a plurality of detector cells form separate columns, or channels, and the columns are arranged in rows. Each row of detectors forms a separate slice. For example, a two slice detector has two rows of detector cells, and a four slice detector has four rows of detector cells. During a multislice scan, multiple rows of detector cells are simultaneously impinged by the x-ray beam, and therefore data for several slices is obtained.

Until now, it was believed that to add rows of detector cells to a CT system, significant hardware and software modifications are necessary. Particularly, a data acquisition system typically samples analog data from each detector cell and converts the data to digital signals for subsequent processing. Therefore, when adding detector cell rows to a detector array, the data acquisition system must be modified to sample data from the additional detector cells. For example, for a two slice system, the data acquisition system must be modified to sample twice as many detector cells compared to a single slice system. Similarly, for a four slice system, the data acquisition system must be modified to sample four times as many detector cells compared to a single slice system.

By increasing the number of detector cells, the amount of data which must be transmitted across the gantry slip ring is increased. Such increased data preferably is transmitted across the slip ring within the same time frame at which data from a system with fewer detector cells is transmitted, and therefore, where increasing the number of detector cells, the data transmission rate across the slip ring typically must be increased.

It would be desirable to add detector cell rows to a CT system without requiring significant software and hardware modifications to known systems. It also would be desirable to provide such a multi-row system without degrading overall image quality.

SUMMARY OF THE INVENTION

These and other objects may be attained by a combination of double and triple cell ganging which resolves any incompatibility between the number of detector channels and the lower number of DAS channels without requiring any significant hardware and software changes. In one specific embodiment, the detector cells (1 mm in width outside the center field of view number 1 ($FOV_1$)) on one side of the detector are wired in pairs, i.e., ganged, to form sets of 2 mm channels, and on the other side of the detector outside the FOV, some detector cells are wired together, i.e., ganged, to form sets of 3 mm channels and some detector cells are ganged to form sets of 2 mm channels. Such ganging of detector cells avoids having to make any significant hardware and software changes to known multislice CT systems.

Further, to avoid objectionable artifacts and resolution degradation in the combination of double and triple cell ganging as described above, redundant sampling patterns are utilized in the data collection. Particularly, in any data set collected with 360° gantry rotation, there exists two complete data sets, and as explained below, no clear boundary can be observed after weighting. A weighting algorithm which under-weights the contributions from the triple cells and over-weights the contribution from the corresponding double cells can be utilized. For example, a weighting factor $\alpha(0 \leq \alpha < 1)$ can be assigned to the triple cell channel and a weighting factor $2-\alpha$ can be assigned to the corresponding double cell channels. The weights in the $\gamma$ direction should be continuous and differentiable to avoid artifacts. Therefore, a smooth transition zoom should exist between the weights of the double cells and the weights of the neighboring triple cells. Similar weights can be applied to the single-double cell region.

The above described combination of double and triple cell ganging provides that detector cell rows can be added to a CT system without requiring significant software and hardware modifications to known systems. In addition, and with the above described weighting method, such combination of double and triple cell ganging does not significantly degrade overall image quality.

DETAILED DESCRIPTION OF THE DRAWINGS

Figure 1:
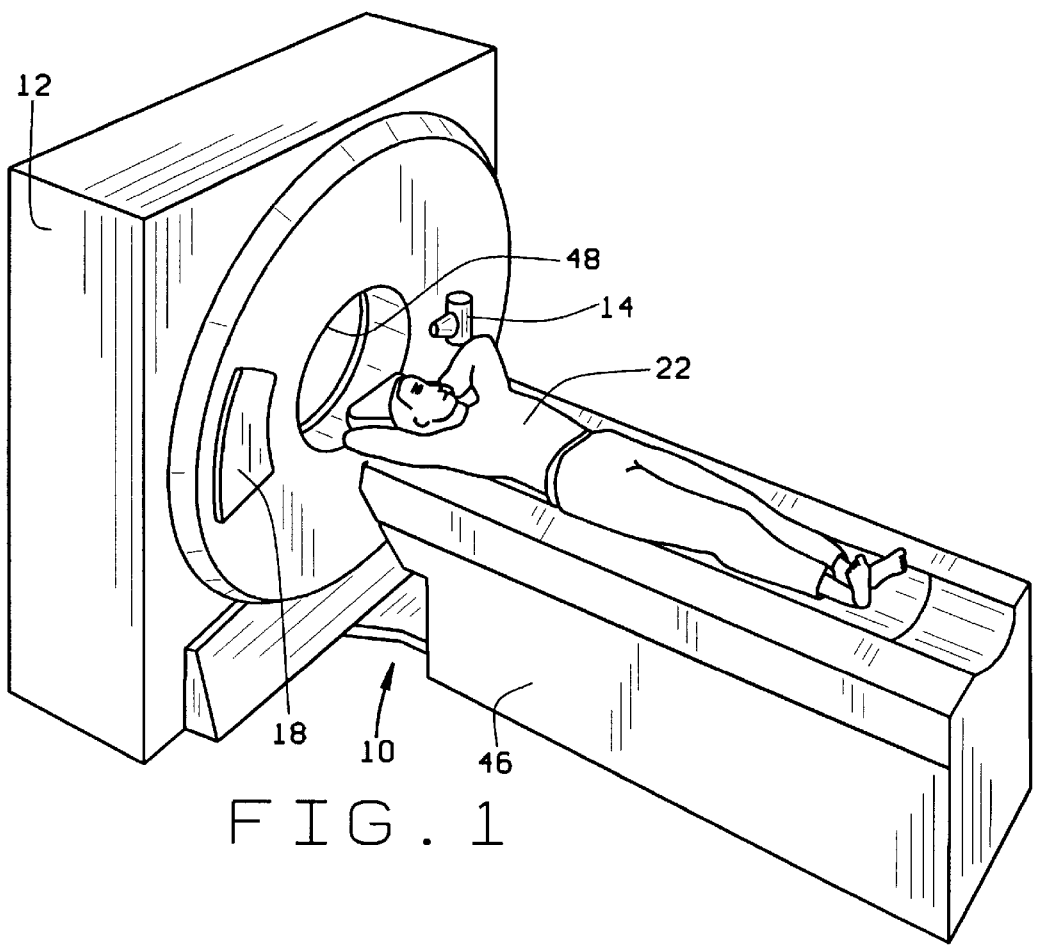
FIG. 1 is a pictorial view of a CT imaging system.
Figure 2:
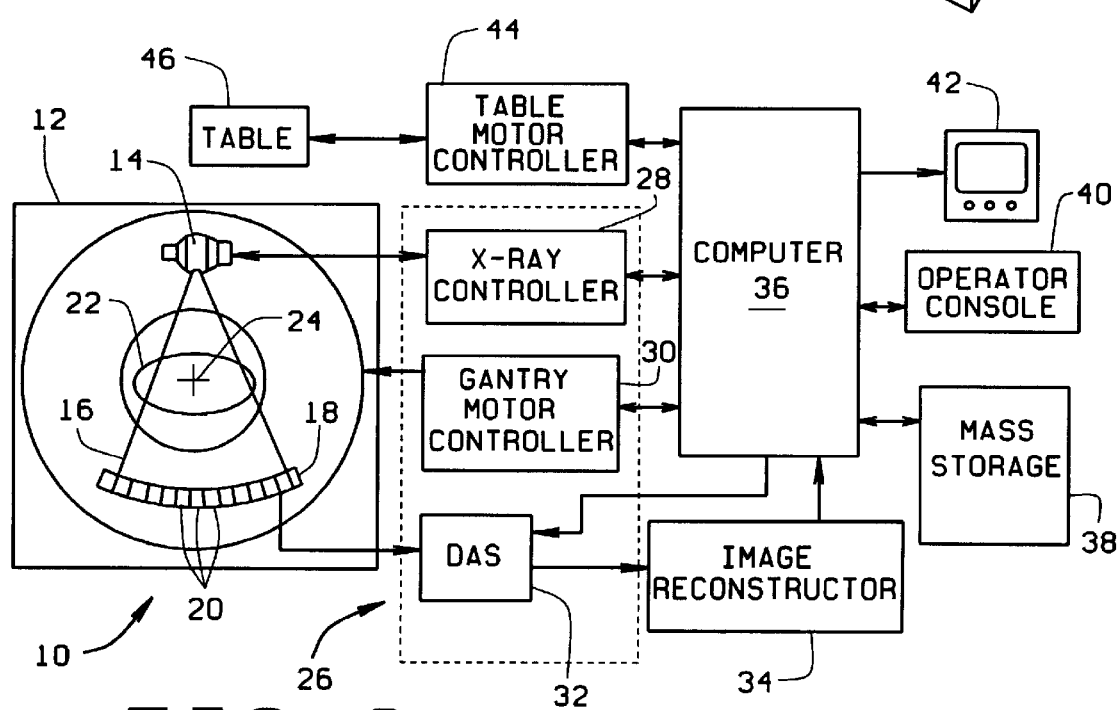
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38. Computer 36 includes a processor, and in one embodiment of the present invention, the processor assigns weights to data collected by DAS 32 as described below in more detail.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The known helical reconstruction algorithms may generally be classified as Helical Extrapolative (HE) or Helical Interpolative (HI) algorithms. These algorithms typically apply a weighting factor to the projection data in order to reconstruct an image. This weighting factor is generally based on both the fan angle and view angle.

The following description of ganged detector arrays sometimes refers specifically to multislice CT scanners, which typically include detector arrays having two, four, or more rows of detector elements, or detector cells. The ganged detector arrays and signal estimation, however, are not limited to practice in connection with only two and four slice scanners and may be used with other multislice CT scanners having more or fewer detector cell rows. In addition, the cell ganging described below can be used in a single slice detector to reduce the costs of the DAS, and the detector cell ganging may also be used in conjunction with axial scans, i.e., in a step-and-shoot mode.

In accordance with one embodiment of the present invention, and in a multislice detector, the incompatibility between the number of detector channels and the lower number of DAS channels is overcome without requiring any significant hardware and software changes by ganging detector channels. More particularly, and referring to FIG. 3, the detector cells in Region 1 on one side of the detector outside the FOV are wired in pairs, i.e., ganged, to form sets of 2 mm channels. In Region 2 on the other side of the detector outside the FOV, the detector cells are wired together, i.e., ganged, to form sets of both 2 mm and 3 mm channels. Such combination of double and triple cell ganging avoids having to make any significant hardware and software changes to known multislice CT systems.

Particularly, the first step in the reconstruction is to "un-gang" cells to obtain single cell data. This step is performed after some preliminary calibration steps such as offset correction. The "un-gang" process is essentially an interpolation process. For example, a Lagrange interpolater can be used. Although the single cell reading can be estimated from double/triple cells, a significant lose of resolution will occur. As a result, some aliasing artifacts will be present.

To avoid objectionable artifacts and resolution degradation in the combination of double and triple cell ganging as described above, redundant sampling patterns are utilized in the data collection. Still referring to FIG. 3, cell A at the boundary between Region 1 and the FOV is located at a different distance from the iso center (ISO) than cell B at the boundary between Region 2 and the FOV. As a result, no clear boundary will be observed after weighting. Particularly, in any data set collected with 360° gantry rotation, there exists two complete data sets. The duplicated sampling pairs satisfy the following relationship:

$$\begin{cases} \beta_2 = \beta_1 + \pi + 2\gamma_1, \text{ and} \\ \quad \gamma_2 = -\gamma_1, \end{cases} \quad (1)$$

where $\beta_1$ and $\beta_2$ are the view angles, and $\gamma_1$ and $\gamma_2$ are the fan angles of the two samples. The sample pairs are always located on the opposite side of the detector. The complementary sample pairs corresponding to the triple cells of the right hand side of the detector are the double cells located on the left hand side.

Therefore, a weighting scheme that under-weights the contributions from the triple cells and over-weights the contribution from the corresponding double cells can be utilized. For example, a weighting factor $\alpha(0 \leq \alpha < 1)$ can be assigned to the triple cell channel and a weighting factor $2-\alpha$ can be assigned to the corresponding double cell channels. The weights in the $\gamma$ direction should be continuous and differentiable to avoid artifacts. Therefore, a smooth transition zoom should exist between the weights of the double cells and the weights of the neighboring triple cells.

Figure 3:
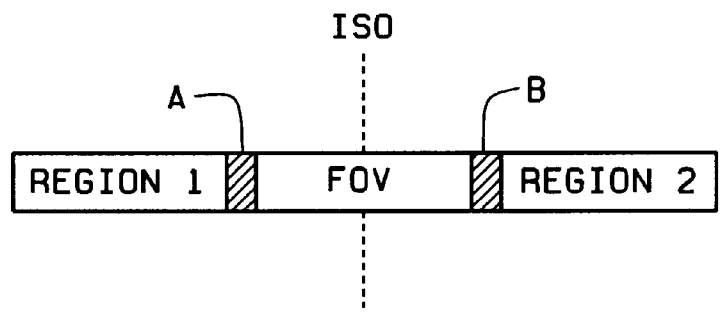
FIG. 3 illustrates, in schematic form, cell ganging in accordance with one embodiment of the present invention.
Figure 4:
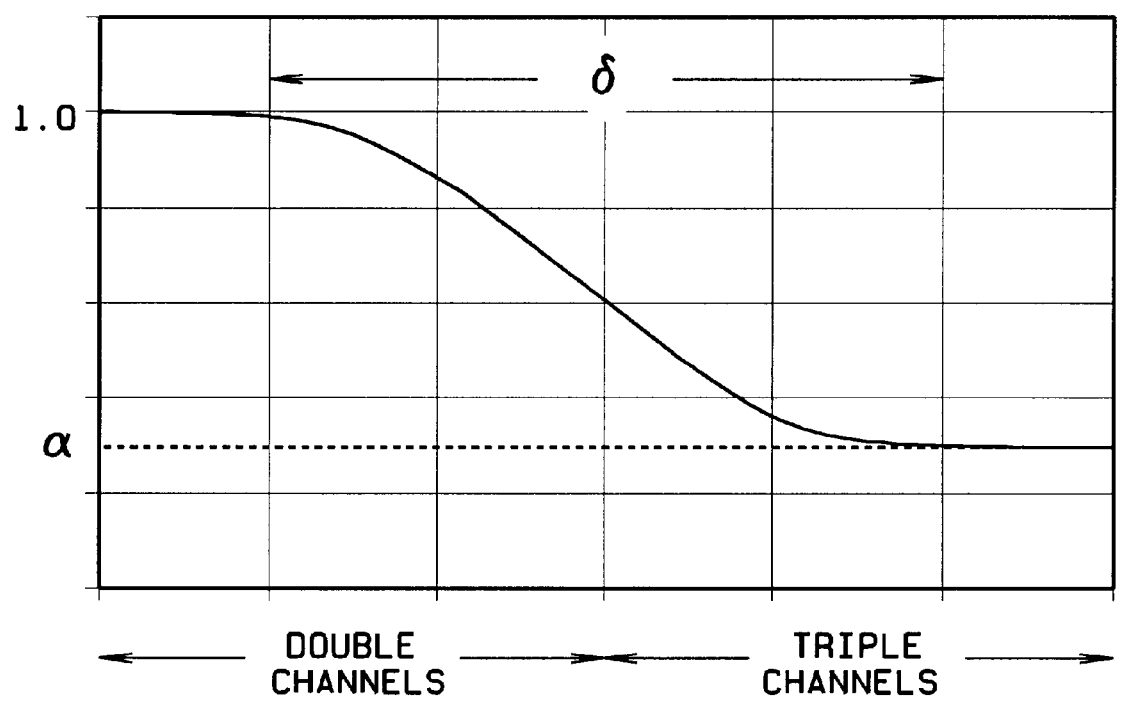
FIG. 4 illustrates one embodiment of a weight curve.

For example, FIG. 3 illustrates one embodiment of a weight curve. The double channels forming complimentary sampling pairs have weights of 2-w. For the transition from the double (w=1) to the triple cell channels, the following weights can be assigned:

$$w(x) = 1 - (1-a)\left[3\left(\frac{x}{\delta}\right)^2 - 2\left(\frac{x}{\delta}\right)^3\right] \quad 0 \leq x \leq \delta \quad (2)$$

where $\delta$ is the transition width, and x is chosen so that $x=\delta$ at the double-triple cell boundary. The triple to double cell transition is a simple reflection of the above equation. Similar weights can be applied to double/single cell pairs.

The above described combination of double and triple cell ganging provides that detector cell rows can be added to a CT system without requiring significant software and hardware modifications to known systems. In addition, and with the above described weighting method, such combination of double and triple cell ganging does not significantly degrade overall image quality.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Accordingly, the spirit and scope of the invention are to be limited only by the terms of the appended claims.

What is claimed is:

1. A detector for a computed tomography system, said detector comprising:

a plurality of detector cells;

a first set of detector cells located within a field of view;

a second set of detector cells located on a first side of said field of view, at least some of said detector cells in said second set N ganged, where N is greater than or equal to one; and a third set of detector cells located on a second side of said field of view, at least some of said detector cells in said third set M ganged, where M is greater than N.

2. A detector in accordance with claim 1 wherein at least some detector cells in said third set are N ganged.

3. A detector in accordance with claim 1 wherein N=2 and M=3.

4. A detector in accordance with claim 1 wherein N=1 and M=2.

5. A detector in accordance with claim 1 wherein said detector cells have a channel width of about 1 mm, and said N ganged detector cells have a channel width of about N mm and said M ganged detector cells have a channel width of about M mm.

6. A detector in accordance with claim 1 wherein said detector is a multislice detector.

7. A detector in accordance with claim 6 wherein said multislice array comprises 2 rows of detector cells.

8. A detector array in accordance with claim 6 wherein said multislice array comprises 4 rows of detector cells.

9. A detector in accordance with claim 1 wherein said detector is a single slice detector.

10. A computed tomography system, comprising:

a detector comprising a plurality of detector cells, a first set of detector cells located within a field of view, a second set of detector cells located on a first side of said field of view, at least some of said detector cells in said second set N ganged, where N is greater than or equal to one, and a third set of detector cells located on a second side of said field of view, at least some of said detector cells in said third set M ganged, where M is greater than N; and a data acquisition system coupled to said detector array.

11. A computed tomography system in accordance with claim 10 further comprising a processor coupled to said data acquisition system, said processor configured to under-weight data contributions from said M ganged cells and to over-weight data contributions from said N ganged cells.

12. A computed tomography system in accordance with claim 10 further comprising a processor coupled to said data acquisition system, said processor configured to apply a weighting factor of $\alpha(0 \leq \alpha < 1)$ to said M ganged cells and a weighting factor of $2-\alpha$ to said N ganged cell.

13. A computed tomography system in accordance with claim 12 wherein a smooth transition zone is provided between said weighting factor of said N ganged cells and said weighting factor of said M ganged cells.

14. A computed tomography system in accordance with claim 13 wherein for said transition zone between said N ganged cells and said M ganged cells, a weighting factor of in accordance with:

$$w(x) = 1 - (1-a)\left[3\left(\frac{x}{\delta}\right)^2 - 2\left(\frac{x}{\delta}\right)^3\right] \quad 0 \leq x \leq \delta$$

is applied, where $\delta$ is the transition width, and x is chosen so that $x=\delta$ at the N-M cell boundary.

15. A computed tomography system in accordance with claim 10 wherein said detector cells have a channel width of about 1 mm, and said N ganged detector cells have a channel width of about N mm and said M ganged detector cells have a channel width of about M mm.

16. A computed tomography system in accordance with claim 10 wherein said detector is a multislice array.

17. A computed tomography system in accordance with claim 10 wherein said detector is a single slice detector.

* * * * *